United States Patent [19]

Eisentraut et al.

[11] 4,324,758

[45] Apr. 13, 1982

[54] ANALYSIS OF LUBRICATING OILS FOR IRON CONTENT

[75] Inventors: Kent J. Eisentraut, Xenia; William D. Ross, Eaton; William J. Hillan, Kettering; Joseph J. Brooks, Centerville, all of Ohio; Thomas G. Duffy, Jacksonville, Fla.

[73] Assignee: The United States of America as represented by the Secretary of the Air Force, Washington, D.C.

[21] Appl. No.: 141,500

[22] Filed: Apr. 18, 1980

Related U.S. Application Data

[62] Division of Ser. No. 29,586, Apr. 12, 1979, Pat. No. 4,238,197.

[51] Int. Cl.³ ............................................ G01N 33/28
[52] U.S. Cl. ..................................... 422/61; 141/100; 141/104; 222/144; 422/68
[58] Field of Search ................ 422/61, 64, 68; 141/9, 141/100, 104, 284; 128/218 R, 218 G, 218 M; 222/135, 144

[56] References Cited

U.S. PATENT DOCUMENTS 2,768,879 10/1956 Hewson .................................. 422/64
3,223,485 12/1965 Ferrari et al. ......................... 422/64
3,594,129 7/1971 Jones ..................................... 422/64
3,713,779 1/1973 Sirago et al. .......................... 422/61
3,715,189 2/1973 Nighohossian et al. .............. 422/61
4,203,725 5/1980 Snowden et al. ................. 422/61 X
4,225,558 9/1980 Peterson et al. .................. 422/61 X

FOREIGN PATENT DOCUMENTS 322364 11/1972 U.S.S.R. ........................... 23/230 M

OTHER PUBLICATIONS

Daus, L. L., "Examination of Used Crankcase Oil", Refined & Natural Gasoline Manufacturer, vol. 21, No. 4, 4/42, pp. 63–66482.

Primary Examiner—Barry Richman
Attorney, Agent, or Firm—Donald J. Singer; William J. O'Brien

[57] ABSTRACT

An apparatus for analyzing a used lubricating oil for iron wear metal content which comprises a series of containers, at least one of which is adapted for holding a test sample material while the remaining containers are adapted for holding 3 separate reagent sample materials. Also included are a reaction chamber, means for transferring the test sample material and the reagent materials from the series of containers to the reaction chamber which may also function as a test cell.

2 Claims, 17 Drawing Figures

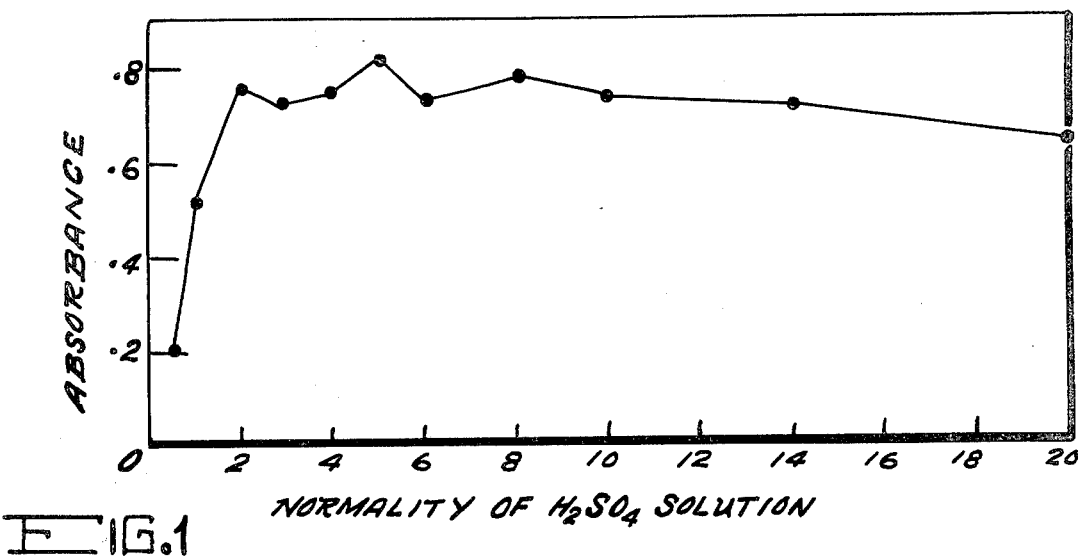
FIG.1
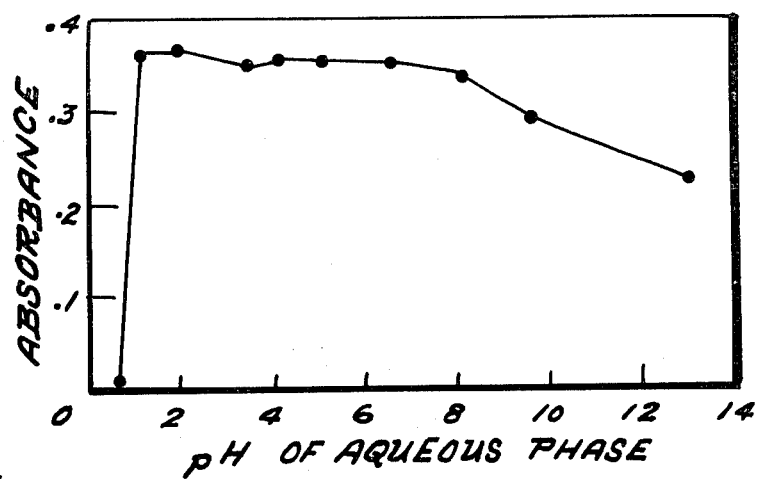
FIG.2
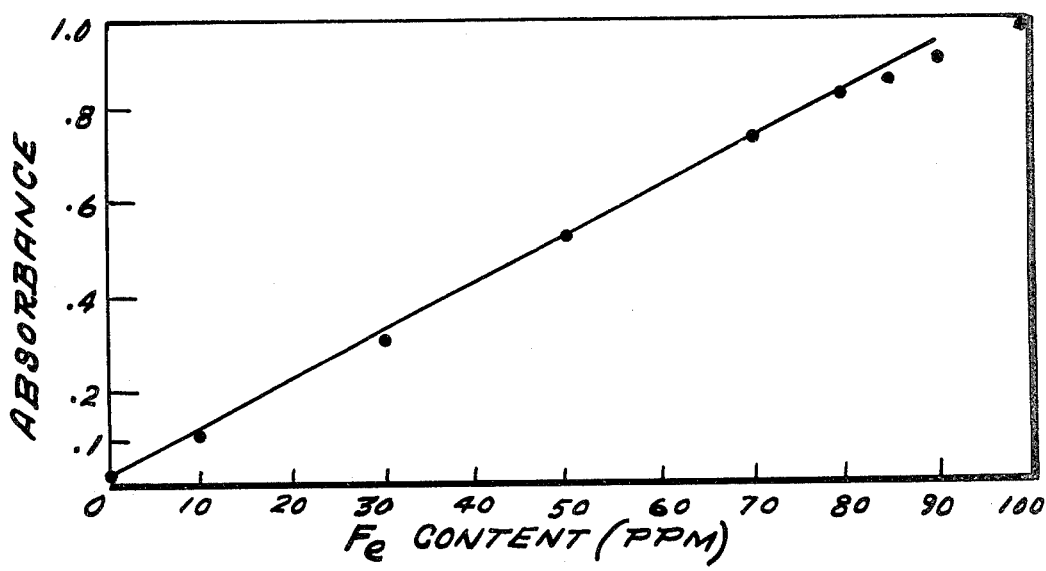

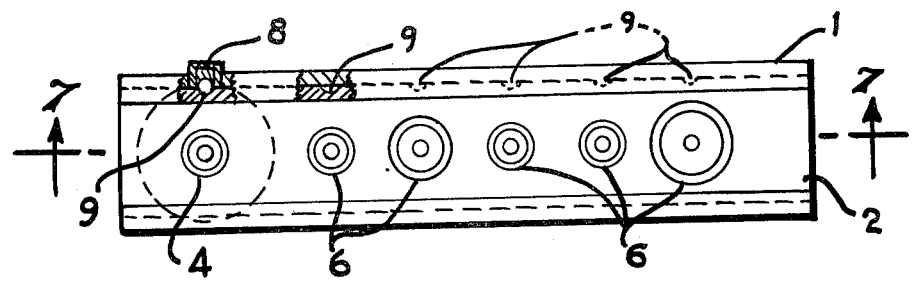
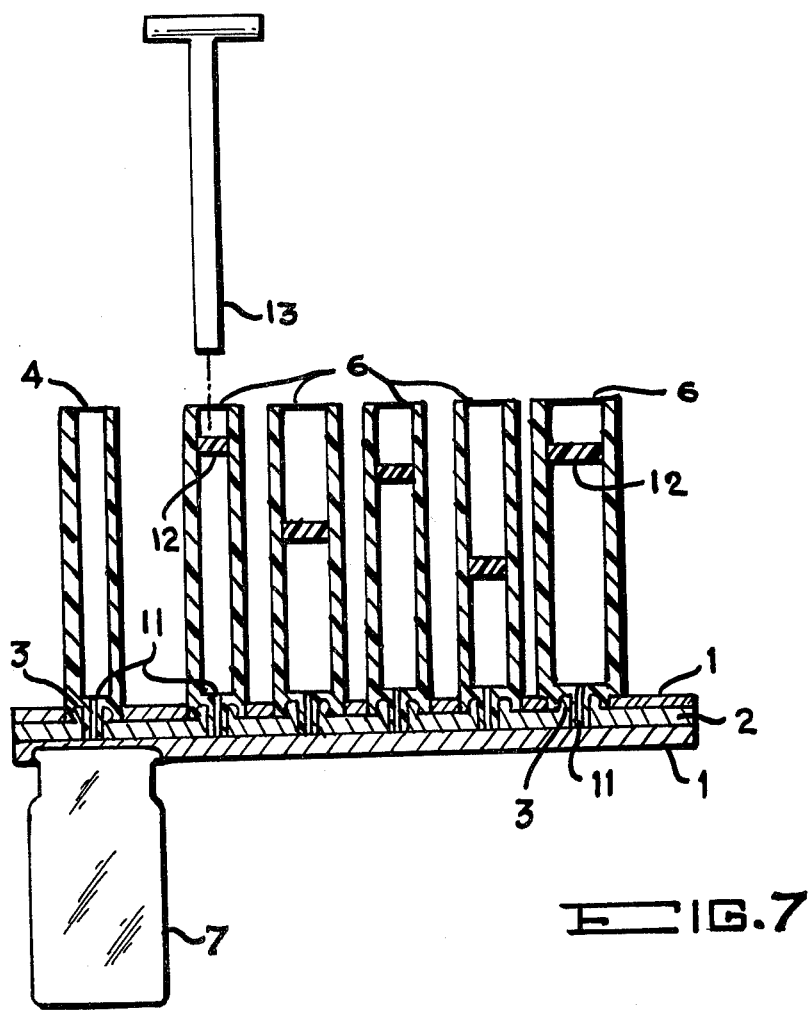

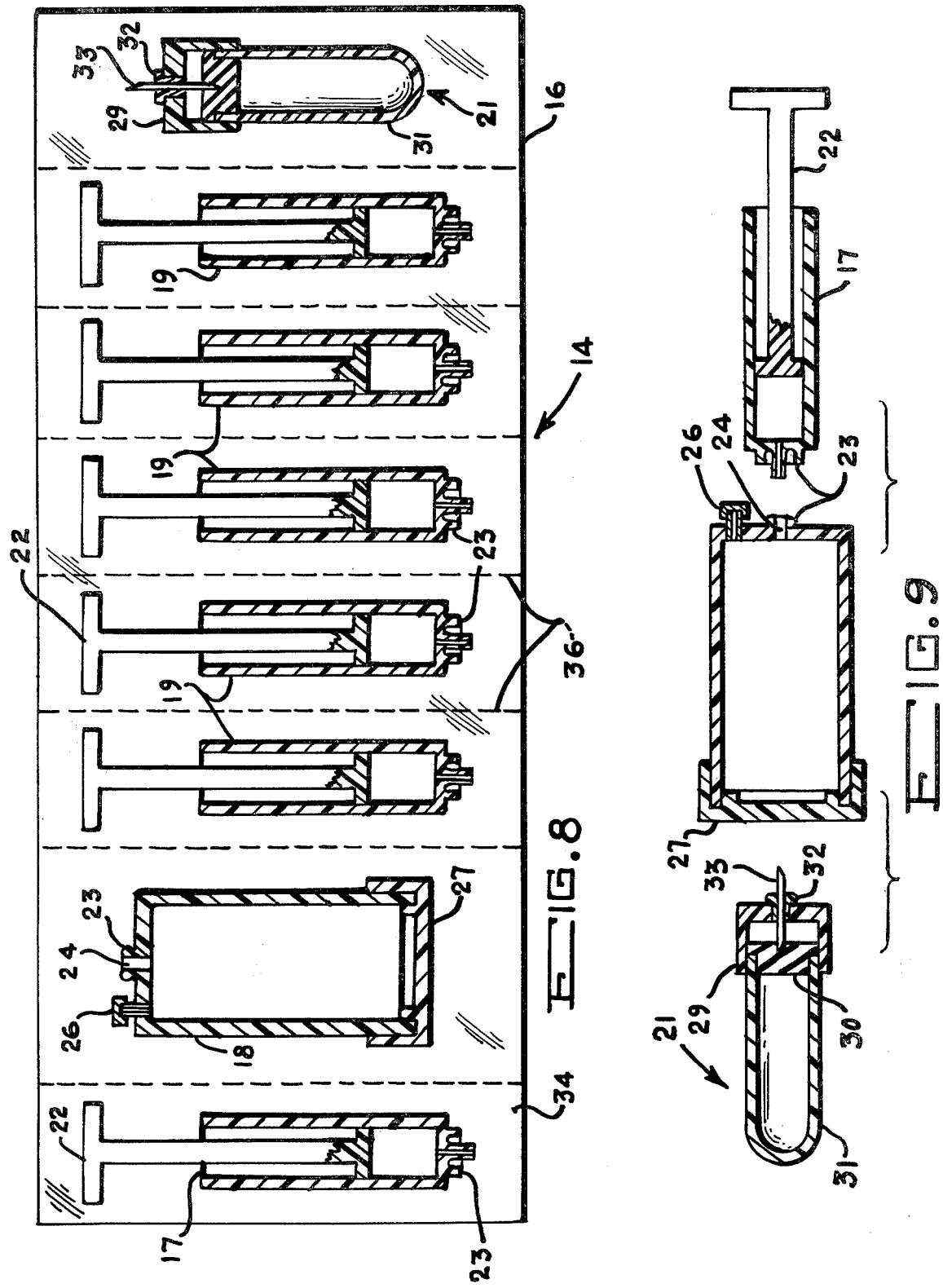

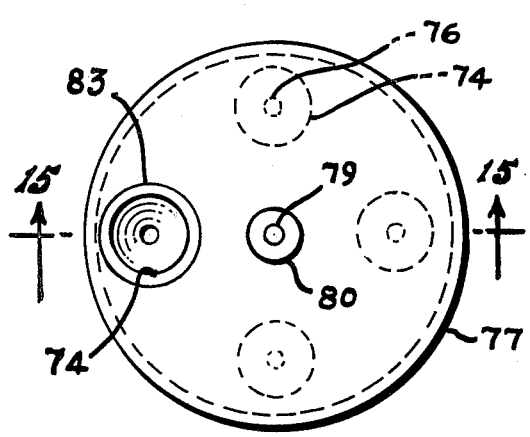
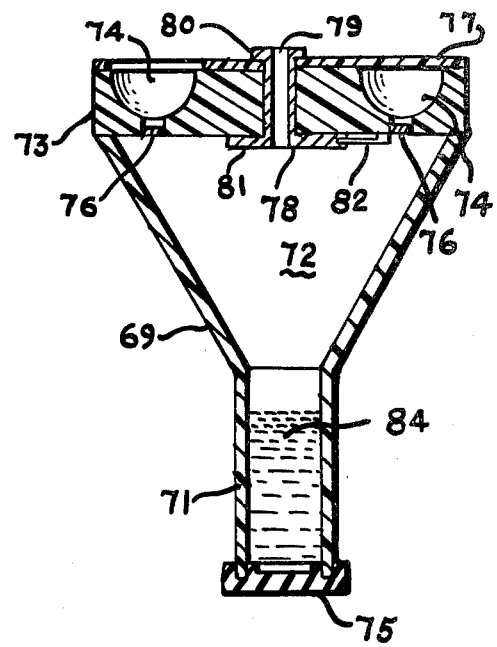
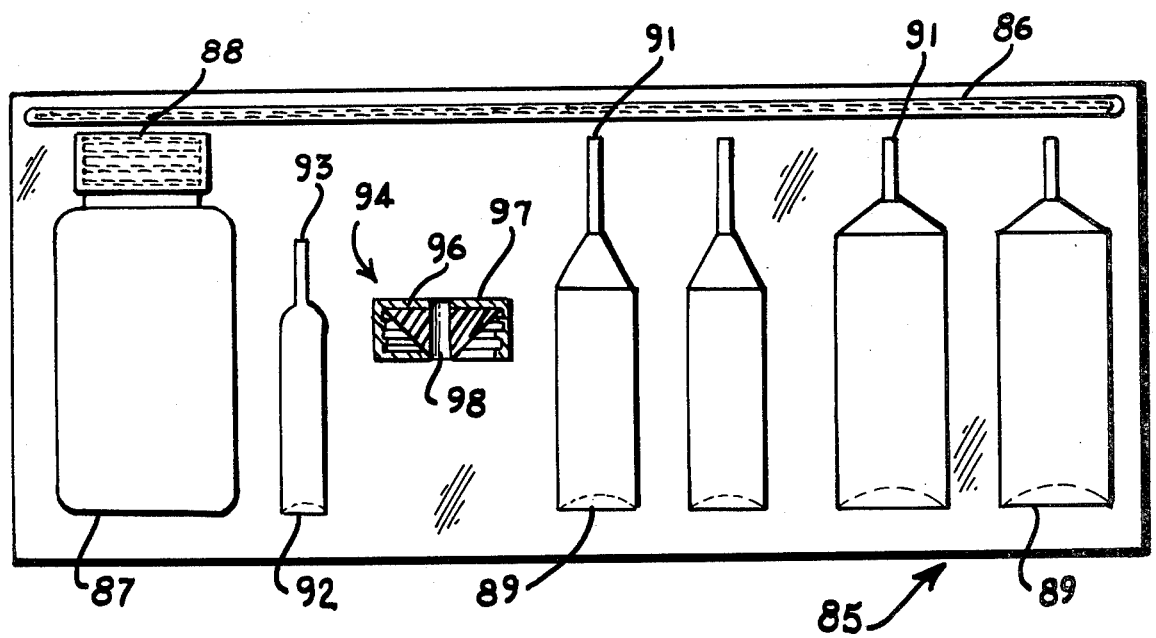

ANALYSIS OF LUBRICATING OILS FOR IRON CONTENT

RIGHTS OF THE GOVERNMENT

The invention described herein may be manufactured and used by or for the Government of the United States for all governmental purposes without the payment of any royalty.

CROSS REFERENCE TO RELATED APPLICATION

This application is a divisional of U.S. Pat. Application Ser. No. 29,586, filed Apr. 12, 1979 and issued as U.S. Pat. No. 4,238,197 on Dec. 9, 1980.

FIELD OF THE INVENTION

This invention relates to a method for determining the amount of iron present in lubricating oil. In one aspect, it relates to apparatus for analyzing lubricating oils for iron content.

BACKGROUND OF THE INVENTION

As is well known, lubricating oils are employed to minimize the wear between the moving parts of machinery. However, in spite of the most effective lubrication, wear does occur as evidenced by the congregation of minute metal particles, particularly iron particles, in the oil. A knowledge of the quantity of iron particles in a lubricating oil, as well as the rate of increase in the quantity, provides important information as regards a particular piece of machinery. Although the quantities may be small, e.g., on the order of 5 to 100 parts per million, experience may dictate that a certain amount indicates a failure condition or a trend toward such a condition.

In an aircraft engine, it is particularly important to be able to predict when engine wear, as evidenced by the presence of iron in particulate and soluble form in its lubricating oil, is approaching an undesirable level. At the present time, this information is obtained by removing an oil sample from the engine and sending it to a laboratory where a highly trained technician analyzes the sample for iron, using an atomic absorption spectrophotometer. This procedure is expensive and time consuming, resulting in a long delay between sample removal and the time corrective action, as dictated by the analytical results, can be taken.

It is an object of this invention, therefore, to provide an improved method for determining the quantity of iron wear metal present in lubricating oils in both particulate and dissolved forms.

Another object of the invention is to provide a method for conducting a rapid, on-the-spot, quantitative test for a major wear metal contained in lubricating oils.

A further object of the invention is to provide apparatus, which may be in the form of a kit, for carrying out the quantitative analysis of iron in lubricating oils.

A still further object of this invention is to provide articles of manufacture which incorporate components used in the practice of the analytical method of this invention.

Other objects and advantages of the invention will become apparent to those skilled in the art upon consideration of the accompanying disclosure and the drawing, in which:

FIG. 1 is a graph that shows the effect of acid concentration on the extraction of iron particles from lubricating oils;

FIG. 2 is a graph that shows the effect of pH on the color formation of bathophenanthroline disulfonic acid in aqueous phase;

FIG. 3 is a calibration curve for D12 Spectrometric Oil Standards, using 0.1000 g bathophenanthroline disulfonic acid in 10 ml distilled water;

FIGS. 6–17 illustrate schematically apparatus and articles of manufacture that can be used in determining the amount of iron wear metal in a lubricating oil sample.

SUMMARY OF THE INVENTION

Figure 4:
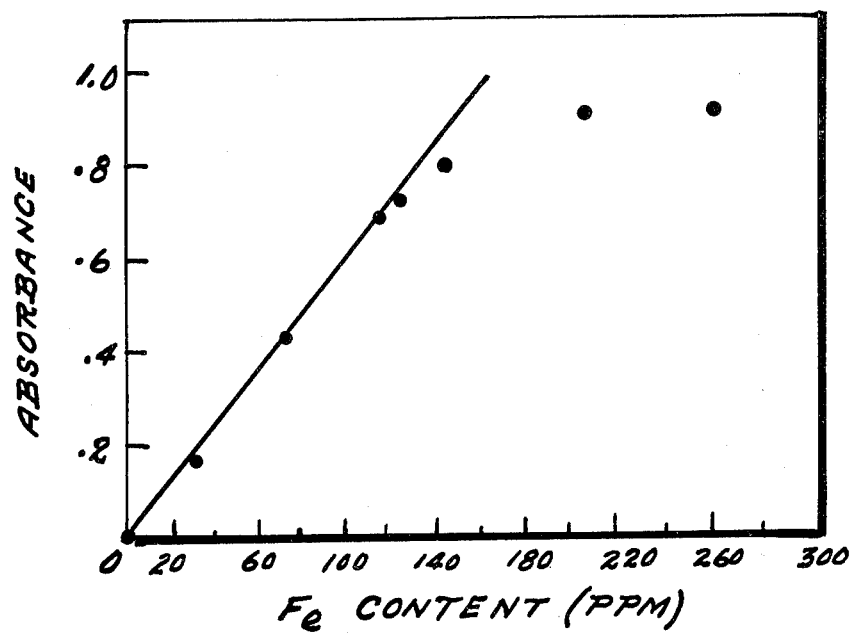
FIG. 4 is a calibration curve for MIL-L-7808 type oil containing only iron, using 0.1000 g bathophenanthroline disulfonic acid in 10 ml distilled water.

The present invention resides in a method for analyzing a lubricating oil for iron wear metal content by following a solvent extraction-chelation procedure. Broadly speaking, the method comprises the steps of extracting all of the iron in a sample of the lubricating oil into an oil immiscible layer, adding buffering and reducing agents, and reacting the iron in the solution with a chelating agent to form a red complex indicative of the iron content.

In a more specific embodiment of the method of this invention, a solution of concentrated sulfuric acid in distilled water and ethanol, isoamyl alcohol, a solution of sodium acetate and hydroxylamine hydrochloride in distilled water, and a solution of an alkali metal salt of bathophenanthroline disulfonic acid in distilled water is thoroughly mixed with a sample of lubricating oil. After allowing oil and colored aqueous phases to separate, the colored phase is recovered and placed in a test cell. Distilled water is then added to the cell, and the solution contained therein is mixed to obtain a uniform color. The solution is finally tested on a colorimeter at 530 nm or compared visually with aqueous standards on a color chart to give a measurement of the amount of iron contained in the oil sample. A wavelength of about 530 nm is used because it is the wavelength at which maximum absorbance for the indicator complex occurs.

In an even more specific embodiment, a solution of concentrated sulfuric acid in distilled water and ethanol is thoroughly mixed with a sample of a lubricating oil. After allowing the oil phase and the oil immiscible phase to separate, isoamyl alcohol is mixed with the solution. The phases are again allowed to separate followed by the addition of a solution of sodium acetate and hydroxylamine hydrochloride in distilled water. The resulting mixture is thoroughly mixed and then allowed to separate into phases. A solution of bathophenanthroline disulfonic acid disodium salt in distilled water is added next, and after a thorough mixing the solution is again allowed to separate into phases. A portion of the colored aqueous phase is withdrawn, introduced into a test cell, and tested as described in the preceding paragraph.

In general, the amount of the various materials used in carrying out the method are comparatively small, measured quantities. FIGS. 1 to 5 show graphically the results of tests that have been conducted for the purpose of determining parameters for conducting the method.

A one milliliter sample of used lubricating oil is usually utilized, and the quantities of the several reagents are employed in measured amounts that conform to the small sample size or are dependent upon other factors. In FIG. 1, there is depicted graphically the effect of sulfuric acid concentration on the extraction of iron particles from lubricating oil. As shown from the graph, 1 to 20 N, preferably 2 to 8 N, acid solutions are effective in extracting the iron from the oil. The ethanol contained in the solution facilitates the reaction between the acid and large iron particles and usually comprises about 10 to 50 volume percent of the total solution. About one milliliter of the acid solution is generally utilized in extracting the iron from the oil sample. However, it is within the scope of the invention to use smaller and larger amounts depending upon the normality of the solution and the amount of iron that the oil may contain. In general, higher acid concentrations are used where large iron particles may be present.

The isoamyl alcohol is added in an amount sufficient to prevent the formation of emulsions. The addition of about 2 milliliters of the deemulsifier has been found to be sufficient for its intended purposes.

In FIG. 2, a graph is set forth that shows the effect of pH on the color formation of bathophenantroline disulfonic acid in aqueous phase. As seen from the graph, the highest color intensity is obtained at a pH of 1 to 7 although a pH as high as 13 can be used. Accordingly, it is usually preferred to use a solution containing an amount of the sodium acetate buffer that is sufficient to provide a pH of about 1 to 7. A reducing agent, namely, hydroxylamine hydrochloride, is contained in solution with the buffer. The solution contains an amount of the reducing agent that is sufficient to reduce $Fe^{+++}$ to $Fe^{++}$. A buffer-reducing solution containing 30 grams of sodium acetate and 20 grams of hydroxylamine hydrochloride dissolved in distilled water by diluting to 100 milliliters has been found to be satisfactory for a 1 N sulfuric acid solution. However, at a higher normality, it is necessary to increase the amount of the sodium acetate buffer. For example, when using a 2.7 N acid solution, 45 grams of sodium acetate is added. About one milliliter of the buffer-reducing solution is employed in conducting the analysis. It is to be understood that the buffer and reducing agent can be introduced in separate solutions. This latter procedure is preferred where the buffer-reducing solution is to be stored for longer than 48 hours in order to avoid reaction between the buffer and reducing agent.

Figure 5:
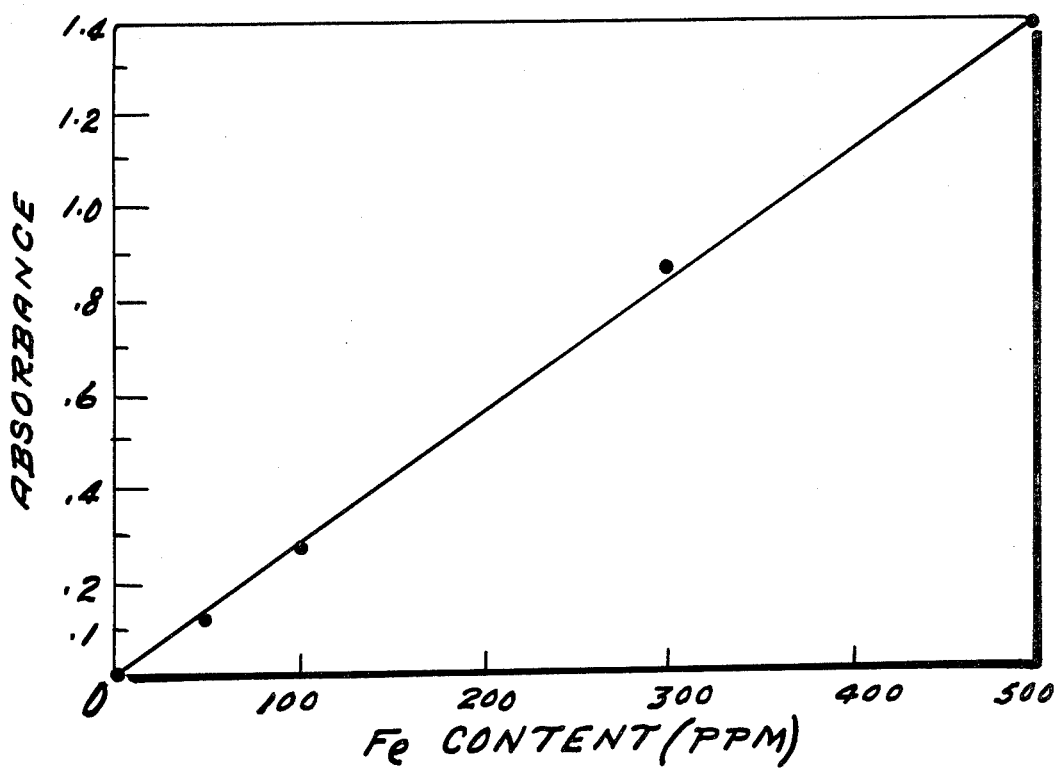
FIG. 5 is a calibration curve for iron content in synthetic lubricating oils, using 0.5 gram bathophenanthroline disulfonic acid in 10 ml distilled water.

The indicator or complexing agent used in the present method is bathophenanthroline disulfonic acid or the alkali metal salt thereof. It is often preferred to use bathophenanthroline disulfonic acid disodium salt although the potassium and lithium salts can also be advantageously used. The amount of the indicator used will depend upon the iron content of the lubricating oil sample. In other words the higher the iron content to be analyzed for in a lubricating oil sample the greater is the amount of indicator required. A solution containing about 0.05 to 0.5 gram of indicator dissolved in 10 milliliters of distilled water generally meets any analytical requirements that may be encountered. A preferred solution is one containing 0.1000 gram of indicator dissolved in 10 milliliters of distilled water. In FIG. 3, a calibration curve is shown for D12 Spectrometric Oil Standards, using 0.1000 gram bathophenanthroline disulfonic acid dissolved in 10 milliliters of distilled water. The oil contains 11 other metals in addition to iron. As seen from the curve, the indicator solution is effective for analyzing up to 80 ppm of iron in the presence of the other metals. A calibration curve is shown in FIG. 4 for MIL-L-7808 type oil containing iron only, using the ame indicator solution. It is seen that in an oil containing only iron the solution is effective for analyzing up to 100 ppm or iron. In FIG. 5, a calibration curve is shown for synthetic lubricating oils, which is derived using aliquots from a stock solution of 0.5 gram of bathophenanthroline disulfonic acid dissolved in 10 milliliters of distilled water. It is seen that the curve is linear and that the indicator solution is effective in analyzing iron contents from 0 to 500 ppm and higher.

In the case of aircraft engines, the main interest is in iron contents from about 0 to 100 ppm. While the present invention is particularly concerned with determining the iron wear metal content of used aircraft lubricating oils, it is also applicable to making such determinations for used oils from other types of engines where the maximum allowable iron contents may be higher, e.g., from 250 to 300 ppm.

In still another embodiment, the present invention is concerned with apparatus which are particularly adapted for carrying out the above-described method. The apparatus are desirably in the form of kits so that they can be used for rapid on-site quantitative analysis of lubricating oils. Broadly speaking, the apparatus comprises six container means, one being for a lubricating oil sample and each of the other five being for a separate reagent; a reaction chamber; means for transferring oil sample and reagents from the container means to the reaction chamber; a test cell; and means for transferring an aqueous phase from the reaction chamber to the test cell.

A more complete understanding of the apparatus can be obtained by referring to the drawing wherein various embodiments are schematically depicted. FIG. 6 is a plan view of apparatus of this invention while FIG. 7 is a cross-sectional view taken along line 7—7 of FIG. 6. As shown in these figures, a base member 1 has a bar or plate member 2 slideably positioned in a groove therein in tongue and groove relationship. Attached to plate 2 by Luerlok fittings 3 or other appropriate fastening devices are oil sample container or tube 4 and reagent containers or tubes 6. A combination reaction chamber-test cell 7 is attached to the underside of base member 1 below oil sample tube 4. A spring-loaded ball bearing 8 mounted in base member 1 cooperates with detents 9 formed in slide bar 2 to provide positive stops for each of the oil and reagent tubes. The base member, bar member, and the oil and reagent tubes can be conveniently formed of a plastic, such as polyethylene. The combination reaction chamber-test cell is formed of a transparent material such as glass.

Passageways 11 communicate the oil and reagent tubes with combination reaction chamber-test cell 7 when positioned thereover. Initially, the lower ends of reagent tubes 6 are sealed, e.g., with a thin layer of silicone sealant or adhesive. After introducing aliquoted reagents into tubes 6, each of the tubes is sealed with a rubber gasket 12. Reading from left to right, the following reagents are charged to the give tubes: (1) acid solution, (2) isoamyl alcohol, (3) buffer-reducing solution, (4) indicator solution, and (5) distilled water.

When analyzing a used lubricating oil for iron content using the apparatus of FIGS. 6 and 7, a measured amount of an oil sample is poured into tube 4 and allowed to flow into chamber 7 through passageway 3. If necessary, plunger 13 can be used to force the oil into the chamber. Slide bar 2 is then moved to the left until ball bearing 8 sets in the next detent 9, thereby bringing reagent tube 6 containing the acid solution in vertical alignment with chamber 7. Plunger 13 is then used to force gasket 12 downwardly against the solution, causing breakage of the seal at the end of passageway 11 and entry of the solution into chamber 7. The solution in chamber 7 is then shaken after which the reagents in the other reagent tubes are successively introduced into chamber 7 in the same manner as the acid solution. After introduction of the reagents, or alternatively after charging each reagent, chamber 7 is shaken to ensure mixing of the materials. An oil phase and a colored aqueous phase are then allowed to separate out in chamber 7. The iron content of the oil sample can now be measured, using the combination reaction chamber-test cell in a direct reading spectrophotometer (not shown).

Reference is now made to FIGS. 8 and 9 which depict another embodiment of this invention. As shown in FIG. 8, a clear plastic container 14 is molded so as to provide eight separate compartments 16. Reading from left to right, the compartments contain an oil dispenser or tube 17, a reaction chamber 18, five reagent dispensers or tubes 19 and a test cell 21. The oil and reagent tubes are each fitted with a removeable plunger 22. The lower end of each of the tubes as well as the upper end of the reaction chamber is provided with a Luerlok type fitting 23. Reagent tubes 19 each contain an aliquoted amount of one of the reagents which are sealed therein at the Luerlok end by a thin layer of silicone sealant or adhesive. Formed in the upper end of the reaction chamber is a passageway 24 which functions as an injection port for introducing oil and reagents into the chamber. The upper end of the reaction chamber is also provided with a pressure relief valve 26 to facilitate addition of the various materials. The lower end of the reaction chamber is closed by means of closure member or septum 27 which is formed of a rubbery material. Test cell 21, which is under a vacuum, has a closure member 29 which slideably fits over the upper end of glass tube 31. A stopper 32 having a hollow transfer needle 33 extending therethrough is threaded into closure member 29. The lower end of the hollow needle extends into rubber gasket 30 which seals the upper end of tube 31.

Plastic container 14 has a clear plastic cover 34 whose edges are heat-sealed to those of the container. The cover is also preferably heat-sealed to ribs of the compartments with the sealed joints 36 being perforated as shown so as to permit individual compartments to be easily separated from one another. The oil and reagent tubes as well as the reaction chamber can be fabricated from any suitable material, e.g., a plastic such as polyethylene. As mentioned above, tube 31 of the test cell is formed of a transparent material such as glass.

An understanding of the manner in which the components shown in FIG. 8 are used in practicing the present method can be obtained by referring to FIG. 9. The same reference numerals are used in FIGS. 8 and 9 to identify the same elements which are shown in section. Oil tube 17 containing a measured amount of used lubricating oil is attached to reaction chamber 18 by means of Luerlok fittings 23. The oil is thereafter forced into the chamber through entry port 24 by depressing plunger 22. After introducing the oil, the oil tube is detached and the five reagent tubes are in a sequence attached to and emptied of their contents into the reaction chamber. After two phases have separated in chamber 18, needle 33 is inserted into the chamber through closure member 27. Closure member 29 is then forced downwardly, causing the lower end of the needle to pierce rubber gasket 30 of tube 31. The lower colored aqueous phase in chamber 18 is thereby readily transferred through the needle into test cell 21 because of the vacuum existing in the cell. By placing the test cell in a direct reading spectrophotometer, the iron content of the oil sample can be determined.

Figure 10:
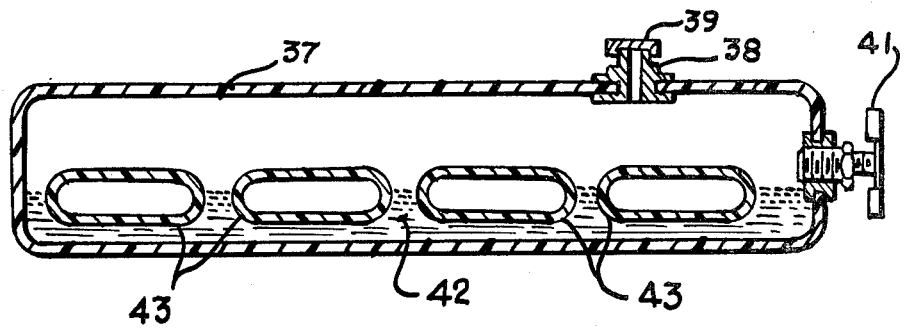

In FIG. 10, an elevational view in cross section of a further embodiment of the invention is illustrated. As shown in this figure, an enclosed container 37 rectangular in shape and formed of a flexible, clear plastic material has injection port 38 positioned in its upper side. The injection port is provided with a snap-on closure member or cap 39 which is maintained in place except when introducing materials into the container. Attached to one end of the container is a locking drain plug 41 which can be a petcock or other suitable device.

Disposed within container 37 is the first reagent, namely, acid solution 42. Capsules 43 positioned within the container in the acid solution each contain one of the other four reagents, namely, isoamyl alcohol, buffer-reducing solution, indicator solution, and distilled water. The capsules are formed of a thin plastic material, such as polyethylene, polypropylene or polymethylmethacrylate, which ruptures when pressure is applied. The capsules may be numbered, color coded, or otherwise marked to identify their contents. Methods for encapsulating materials, such as the reagents, involve procedures that are well known in the art.

The capsules containing reagent are usually placed in the container prior to installation of injection port 38 and drain plug 41 and prior to introduction of the acid solution. Thereafter, halves of the container or portions thereof are heat-sealed or joined with a suitable adhesive. After the capsules are in place and the injection port and drain plug have been installed, the acid solution is introduced through injection port 38 which is then closed with cap 39. Drain plug 41 is, of course, in a closed position at this time. The apparatus is now ready for use in carrying out the present analytical method.

When carrying out the present method in the apparatus of FIG. 10, initially a used oil sample is introduced into container 37 through injection port 38 by means of a syringe or other suitable device. Cap 39 is then reinstalled over the port. The other four reagents are added to the solution in the container by pressing the flexible container so as to rupture or break the capsules and release the various reagents. After breaking the capsules, it is usually desirable to shake the container so as to ensure mixing of the oil and the reagents. The container is then placed in a substantially vertical position whereby an upper oil phase and a lower colored aqueous phase are formed. The aqueous phase is then transferred to a test cell (not shown) by opening drain plug 41. The color intensity of the aqueous phase, which is indicative of iron content, is thereafter measured by a spectrophotometer.

Figure 11:
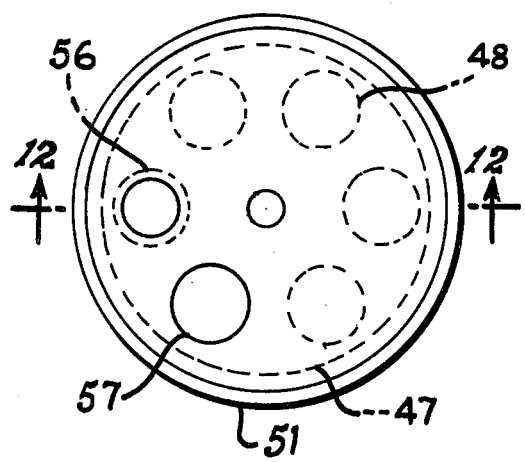
Figure 12:
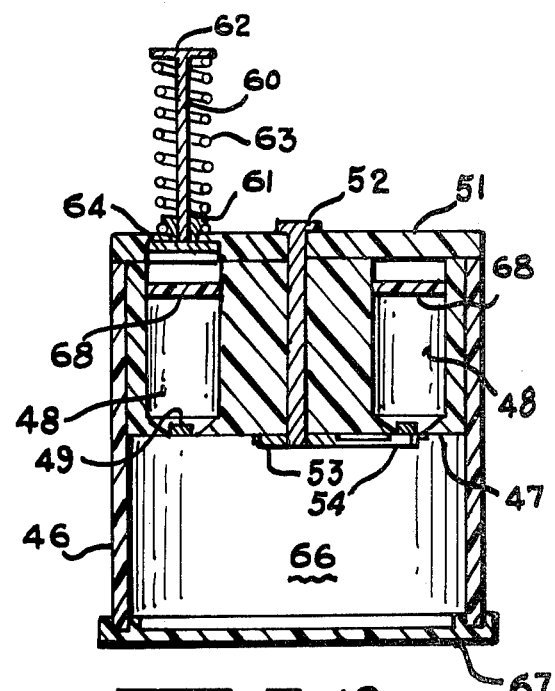

Reference is now made to FIGS. 11 and 12 for an illustration of still another embodiment of the present invention. FIG. 11 is a plan view of the apparatus while FIG. 12 is a cross-sectional view taken along line 12—12 of FIG. 11. As shown in the figures, a cylindrical member 46 has a solid, cylindrical body member 47 positioned in its upper portion. The body member is held in position with its outer wall in contact with the inner wall of the cylinder by means of an adhesive or by screws or bolts (not shown) which pass through the wall of the cylinder into the wall of the body member.

Body member 47 has formed therein six cells 48 in the form of cylindrical cavities having rounded lower ends. The cells are equally spaced with their centers defining a circle whose center coincides with the center of the cylindrical body member. Each of the cells has a small opening in the lower end thereof. In the case of five of the cells which are adjacent to one another and function as receptacles for the five reagents, the openings are sealed with a break-away seal 49 such as a silicone sealant or adhesive. The opening in the sixth cell, which is for the oil sample, is unsealed.

Cylindrical member 46 has a circular top member 51 of about the same diameter positioned on its upper end. Attached to the center of the underside of the top is a shaft 52 which extends down through the center of the body member. The lower end of the shaft has a ratchet wheel 53 connected thereto. The ratchet wheel cooperates with a pawl 54 which is attached to the lower end of the body member. The ratchet wheel and pawl are further illustrated in FIG. 13.

Figure 13:
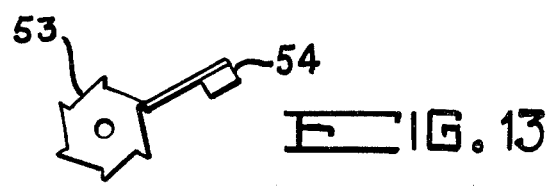

Top member 51 has two circular openings 56 and 57 therein that are adjacent to one another and have about the same diameter as the cells. Opening 56 as illustrated has a spring loaded plunger associated therewith. The plunger comprises a piston 59 with an attached shaft 60 riding in the bushing 61, a handle 62, and a spring 63. When in an extended condition, the spring pressing against handle 62 and the top of circular shoulder 64 maintains the upper side of piston 59 against the underside of the circular shoulder. The underside of piston 59 is in line with or above the underside of top member 51 so as to permit rotation of the plunger when the top is rotated on its shaft. As shown in FIG. 13, the ratchet wheel and pawl are so constructed that the top can be rotated in only one direction (counterclockwise). Furthermore, the teeth on the ratchet wheel are so spaced and the wheel is so attached to the shaft that the top can be stopped with the plunger piston in line with a cell opening.

The lower portion of cylindrical member 46 below body member 47 constitutes reaction chamber 66. The lower end of the reaction chamber is enclosed by closure member or septum 67. The closure member is formed of a rubbery material that can be penetrated by a sharp point. The other principal portions of the apparatus can be conveniently fabricated from a plastic material such as polyethylene.

Prior to use of the apparatus of FIGS. 11 and 12 in the present analytical method, a measured amount of each reagent is introduced into appropriate cells. Referring still to FIGS. 11 and 12, the introduction is carried out by first removing top member 51. This is accomplished by removing septum 67 and ratchet wheel 53 so that the top and plunger can be separated from the body member. Then commencing with the first reagent cell positioned counterclockwise from the oil sample cell, the reagents are charged separately in the following order: (1) acid solution, (2) isoamyl alcohol, (3) buffer-reducing solution, (4) indicator solution, and (5) distilled water. After introduction of each reagent, each cell is fitted with a rubber gasket 68 about the surface of the reagent. The apparatus is then reassembled and top member 51 is rotated so that oil injection port or opening 57 is over the oil sample cell. It is to be understood, of course, that the reagents can be injected initially into their appropriate cells prior to assembly of the apparatus.

With opening 57 in position over the oil sample cell, a sample of used lubricating oil is added to the cell by a pipet or other suitable device. The top is then rotated until the plunger is over the oil sample cell after which the plunger is depressed to as to ensure complete transfer of the oil into reaction chamber 66. The reagents are then added to the reaction chamber in the above-mentioned sequence by rotating the top until the plunger is over the proper reagent cell and then depressing the plunger. The movement of the plunger forces the gaskets downwardly, causing transfer of the reagents into the reaction chamber through broken seals.

After shaking the reaction chamber to ensure thorough mixing, the oil and aqueous phases are allowed to separate. A test cell similar to that shown in FIGS. 8 and 9 is then used to withdraw the colored aqueous phase from reaction chamber 66. By placing the test cell in a direct reading spectrophotometer, the iron content of the oil sample is readily determined.

Reference is now directed to FIGS. 14 and 15 which depict a further embodiment of the present apparatus. FIG. 14 is a plan view of the apparatus while FIG. 15 is a cross-sectional view taken along line 15—15 of FIG. 14. As shown in FIG. 15, an inverted frusto-conical member 69 having a cylindrical member 71 attached to its lower end constitutes a reaction chamber 72. The lower end of the cylindrical member is fitted with closure member or septum 75 which is formed of a rubbery material.

Positioned on the upper end of frusto-conical member 69 is a solid cylindrical body member 73. Four hemispherical, equally spaced cavities 74 are formed in the body member adjacent its periphery. An opening 76 in the bottom of each cavity communicates the cavity with reaction chamber 72. Cylindrical body member 73 has a circular top member 77 of about the same diameter positioned on its upper surface. A hollow shaft 78 with opening 79 extends through the top and body, terminating below the latter member. The upper end of the shaft has a circular shoulder 80 which rests against the upper surface of the top member and holds the shaft in place. The lower end of the hollow shaft has a ratchet wheel 81 connected thereto. The ratchet wheel cooperates with a pawl which is attached to the lower side of the body member. Ratchet wheel 81 and pawl 82 are further illustrated in FIG. 16. The ratchet wheel of FIG. 16 differs from that of FIG. 13 in that it has four teeth rather than six.

As illustrated in FIG. 16, the ratchet wheel and pawl are so constructed that the top can be rotated on its shaft in only one direction (counterclockwise). Furthermore, the teeth on the ratchet wheel are so spaced and the wheel is so attached to the shaft that the top can be stopped with opening 83 therein directly above a cavity.

Before using the apparatus of FIGS. 14 and 15 in practicing the present method, the first reagent 84, i.e., the acid solution, is introduced into reaction chamber 72 through hollow shaft 78. Four capsules or buttons (not shown) each containing one of the other four reagents are individually placed in a cavity. The reagent-containing capsules are placed in the cavities so that reading clockwise they are in the following order: (1) isoamyl alcohol (3) buffer-reducing solution, (3) indicator solution, and (4) distilled water. Now when the top is rotated counterclockwise, opening 83 can be positioned so that the reagents can be introduced into the reaction chamber in the proper sequence. The capsules are formed of a thin plastic material, such as polyethylene, polypropylene or polymethacrylate, which ruptures when finger pressure is applied.

When analyzing for iron in a lubricating oil, a sample of the oil is introduced through hollow shaft 78 into the reaction chamber which already contains acid solution 84. The other four reagents are then added in the above-indicated sequence by rotating the top until opening 83 is over the appropriate cavity and then rupturing the capsule. As a result, the reagents in turn flow through cavity openings 76 into the reaction chamber.

After shaking the reaction chamber to ensure thorough mixing, the oil and aqueous phases are allowed to separate. A test cell similar to that shown in FIGS. 8 and 9 is then used to withdraw the colored aqueous phase by inserting needle 33 through septum 75. The iron content of the oil sample can then be readily determined by placing the test cell in a direct reading spectrophotometer.

In FIG. 17 there is illustrated still another embodiment of this invention in the form of an article of manufacture. The various components are shown as being disposed in a clear plastic container or envelope which is rectangular in shape and may conveniently be a zip lock plastic bag 85 having an elongated opening 86. Container or bottle 87, formed of glass or a transparent plastic material, functions both as a reaction vessel and test cell. The reaction vessel has a screw cap 88 which is conveniently fabricated from polyethylene or other suitable plastic material. The reaction vessel contains the first and second reagents, namely, the sulfuric acid solution and the isoamyl alcohol. Tubes 89 provided with sealed tips 91 contain the other reagents used in practicing the present invention. Rading from left to right, the tubes contain, respectively, the buffer solution, the reducing solution, the indicator solution, and distilled water.

It is noted that in this embodiment, the buffer and reducing solutions are in separate tubes whereas in the previously described embodiments the buffer and reducing agents were included in the same solution. If the materials are to be stored for longer than two or three days, it is preferred that the buffer and reducing solutions be separated. Thus, in the case of the other embodiments, the isoamyl alcohol may be included in the same tube or container as the sulfuric acid solution. The tube or capsule designated for isoamyl alcohol is then used for the buffer solution while the tube or capsule designated for the buffer-reducing solution is used to contain only the reducing solution.

Referring still to FIG. 17, tube 92 has an open narrow tip 93 and a lower open end adapted to fit over the end of a pipet. Cap 94 having an opening therethrough is threaded so as to fit onto the end of bottle 87. Liner 96, substantially in the shape of an inverted cone, is adapted to fit into the opening in cap 94. When cap 94 is screwed onto bottle 87, liner 96 with opening 98 therethrough is held firmly in place by being forced against shoulder or lip 97. Opening 98 is sized so that a tight fit is obtained when tips 91 or 93 are inserted thereinto. The several tubes, open cap and liner, can be fabricated from polyethylene or other suitable plastic material.

When utilizing the various components of FIG. 17 in carrying out the present method, initially cap 88 is removed from bottle 87 containing the acid solution and isoamyl alcohol. Tube 92 is placed on the end of a pipet (not shown) which is then filled with the desired amount of the oil sample. After inserting the tip into the bottle opening, oil is forced from the pipet into bottle 87 by means of a plunger (not shown). Cap 88 is now screwed back onto the bottle, and its contents are thoroughly mixed by shaking, e.g., on a vortex mixer.

After the mixing operation, cap 88 is removed from the bottle and replaced with cap 94 and liner 96. A small portion of tip 91 of the first reagent tube (reading from left to right in FIG. 17) is cut off so as to allow buffer solution to flow therefrom. After inserting the tip of the tube into the opening of the liner, the tube is squeezed so as to force the solution into the bottle. With the tube in place, the bottle is shaken, e.g., for 1 or 2 minutes to ensure good mixing. Because of the tight fit of the tip in the liner opening, an effective seal is provided during the shaking operation. The first reagent tube is then removed, and the procedure is repeated for the second (reducing solution), third (indicator solution), and fourth (distilled water) reagent tubes. The tubes may be color coded or numbered to ensure that the correct sequence is followed.

At the end of the above-described procedure, the open cap with liner is removed and replaced with solid cap 88. After the phases have separated, the color intensity of the aqueous phase in the reaction-test cell (bottle) is measured by a direct reading spectrophotometer.

The spectrophotometer used is a commercially available piece of equipment such as Hack Model DR/2. The instrument is locked into the required wavelength (530 nm). The meter scale is calibrated by using samples containing known amounts of iron so that the scale reads directly in parts per million (ppm) iron.

A more comprehensive understanding of the invention can be obtained by referring to the following illustrative examples which are not intended, however, to be unduly limitative of the invention.

EXAMPLE I

A series of runs was conducted in which various lubricating oil samples were analyzed for iron content by the method of this invention. Control runs were also carried out in which samples of the same oils were analyzed by the conventional technique using an atomic absorption spectrophotometer. The samples were of MIL-L-7808 type lubricating oils removed from type J57-59W engines on KC135 aircraft.

The following reagents were used in making the tests:

(1) 1 N sulfuric acid solution—3 ml of concentrated sulfuric acid in 67 ml of distilled water and 30 ml ethanol;

(2) Isoamyl alcohol (reagent grade);

(3) Buffer-reducing solution—30 g sodium acetate, 20 g hydroxylamine hydrochloride dissolved in distilled water by diluting to 100 ml;

(4) Indicator solution—0.10 g bathophenanthroline disulfonic acid disodium salt dissolved in 10 ml distilled water; and (5) Distilled water.

In each run, one milliliter of used turbine engine oil was placed in a reaction vessel (3 dram vial), and one milliliter of sulfuric acid solution was added. The solution was shaken for about 5 minutes and the phases were allowed to separate. Two milliliters of isoamyl alcohol was added and the solution was shaken for about one minute. After separation of the phases, one milliliters of buffer-reducing solution was added, and the solution was shaken for about one minute. After separation of the phases, one-half milliliter of indicator solution was added, and the solution was shaken for about one minute. The phases were then allowed to separate. A pipet was used to withdraw a one milliliter aliquot of the colored aqueous phase that was introduced into a test cell. Five milliliters of distilled water was added to the test cell and the solution was mixed. The solution was tested on a commercially available colorimeter (Chemtrix 20) at 530 nm. The results obtained in the runs as well as the results of the control runs are set forth below in Table I.

TABLE I

| Sample No. | Operating Hrs since Overhaul | Operating Hrs since Oil change | Fe Content by Atomic Absorption, ppm | Fe Content by Invention Method, ppm |
|---|---|---|---|---|
| J-3 | 1488 | 184 | 2.2 | 1.5 |
| J-4 | 389 | 78 | 3.5 | 3.4 |
| J-15 | 1303 | 241 | 5.2 | 4.3 |
| J-700 | 1828 | 877 | 6.0 | 5.4 |
| J-604 | 2740 | 365 | 7.5 | 5.7 |
| J-790 | 1819 | 372 | 10.0 | 6.7 |
| J-382 | 2284 | 739 | 11.8 | 6.7 |
| J-683 | 1023 | 469 | 11.9 | 7.1 |
| J-259 | 2289 | 115 | 11.0 | 11.6 |
| J-559 | 50 | 11 | 15.1 | 15.2 |
| J-489 | 261 | 261 | 14.8 | 12.4 |
| J-354 | 22 | 22 | 17.5 | 17.7 |
| J-849 | 489 | 100 | 27.0 | 26.0 |
| J-863 | 3288 | 588 | 31.8 | 30.4 |
| J-865 | 3284 | 583 | 35.5 | 33.7 |

EXAMPLE II

Using the same reagents described in Example I, one milliliter of the sulfuric acid solution, two milliliters of isoamyl alcohol, one milliliter of the buffer-reducing solution, and one-half milliliter of the indicator solution are placed in a reaction vessel. One milliliter of used oil is added to the reaction vessel, and the solution is agitated by a vortex stirrer for about one minute. The phases are allowed to separate (about one minute) and one milliliter of the colored phase is drawn off and placed in a test cell. Five milliliters of distilled water is added, and the solution is mixed briefly to obtain a uniform color. The solution is then tested on a colorimeter at 530 nm.

EXAMPLE III

Three series of runs were conducted in which various samples of lubricating oils were analyzed for iron content by the method of this invention. The procedure followed was essentially the same as that described in Example I except as to the normality of the acid solutions used in two of the series of runs. Thus, in the three series 1 N, 2 N and 3 N $H_2SO_4$ solutions were utilized. The results obtained in the runs are set forth below in Table II.

TABLE II

| Sample No. | Iron Content (ppm) | | |
|---|---|---|---|
| | 1N $H_2SO_4$ | 2N $H_2SO_4$ | 3N $H_2SO_4$ |
| H-63 | 16.3 | 22.4 | 26.6 |
| H-65 | 13.5 | 14.9 | 13.3 |
| P-44 | 32.3 | 41.5 | 43.6 |
| P-62 | 21.8 | 26.1 | 29.4 |
| P-64 | 22.3 | 25.0 | 30.4 |
| P-86 | 6.3 | 6.1 | 6.6 |
| P-87 | 2.0 | 3.7 | (1) |
| P-88 | 30.1 | 38.3 | 40.8 |
| P-90 | 8.6 | 10.4 | 12.2 |
| P-91 | 13.9 | 16.9 | 19.5 |
| F-17 | 49.0 | 52.2 | 58.2 |
| F-18 | 41.8 | 47.9 | 44.5 |
| F-23 | 37.9 | 48.4 | 55.9 |
| F-37 | 8.6 | 10.9 | 9.6 |
| F-38 | 3.4 | 3.4 | 2.1 |
| F-39 | 14.1 | 19.6 | 27.1 |
| R-424 | 9.5 | 12.5 | 14.3 |

EXAMPLE IV

A series of runs was conducted in which various samples of lubricating oils were analyzed for iron content by the method of this invention. The procedure followed was essentially the same as that described in Example I except that a 3 N sulfuric acid solution was used. Control runs were also carried out in which samples of the same oils were analyzed by the conventional technique using an atomic absorption spectrophotometer. The results obtained as well as other information are shown hereinafter in Table III.

TABLE III

| Sample Number | Iron Content (ppm) | | Engine Type | Hrs Since Overhaul | Hrs Since Oil Change |
|---|---|---|---|---|---|
| | Atomic Absorption | Invention Method | | | |
| P-44 | 35.1 | 43.6 | J-79 | 55 | 0 |
| P-62 | 26.3 | 29.4 | R-56 | 2027 | 728 |
| P-64 | 26.0 | 30.4 | R-56 | 2058 | 759 |
| P-65 | 15.0 | 15.3 | J-56 | 3173 | 657 |
| P-78 | 11.8 | 9.8 | J-85 | 2202 | 165 |
| P-81 | 6.5 | 3.7 | J-79 | 486 | 9 |
| P-86 | 7.1 | 6.6 | J-79 | 566 | 550 |
| P-87 | 2.9 | 3.7 | F-100 | 271 | 202 |
| P-88 | 33.9 | 40.8 | TF-33 | 6080 | 462 |
| P-90 | 12.4 | 12.2 | J-85 | 452 | 0 |
| P-91 | 11.0 | 19.5 | J-85 | 680 | 0 |
| R-424 | 12.7 | 14.3 | R-56 | 3798 | 2034 |
| R-429 | 6.5 | 5.9 | J-85 | 1773 | 150 |
| R-437 | 2.0 | 1.3 | J-57 | 1511 | 817 |
| R-443 | 7.0 | 6.5 | J-85 | 1815 | 172 |
| R-452 | 3.1 | 2.8 | J-85 | 1540 | — |
| H-51 | 16.8 | 18.7 | R-56 | 1616 | 80 |
| H-58 | 2.0 | 1.4 | F-100 | 3025 | 869 |
| H-63 | 20.7 | 26.6 | J-85 | 2092 | 110 |
| H-64 | 7.6 | 8.2 | J-85 | 430 | 2 |
| H-65 | 12.3 | 13.3 | T-56 | 2031 | 568 |
| H-68 | 7.7 | 7.2 | T-56 | 4537 | 833 |
| F-17 | 30.9 | 58.2 | J-85 | 1982 | 3 |
| F-18 | 60.5 | 44.5 | T-56 | 1633 | 527 |
| F-23 | 16.1 | 55.9 | T-56 | 1123 | 400 |
| F-34 | 6.2 | 5.7 | T-56 | 284 | 284 |
| F-37 | 3.3 | 9.6 | TF-39 | 1863 | 617 |
| F-38 | 3.2 | 2.1 | TF-56 | 1850 | 765 |
| F-39 | 22.0 | 27.1 | TF-56 | 1720 | 130 |

From the foregoing, it is seen that the method of this invention makes it possible to analyze for a major wear metal contained in lubricating oil. The results obtained compare favorably with those derived by the expensive laboratory procedure performed by highly trained technicians using an atomic absorption spectrophotometer. Also, the present method is not limited to the analysis of oil samples containing particles of a maximum size as are the techniques of atomic absorption/atomic emission spectrophotometry. The method can be performed in the field by non-technical personnel, thereby eliminating the long lag time currently experienced between the time the oil sample is removed from the equipment and the time corrective action, as dictated by the analytical results, can be implemented. The method of this invention can be advantageously carried out in the above-described apparatus whose elements can be packaged into inexpensive, portable, self-contained kits which are particularly useful for performing on-site analyses.

As will be evident to those skilled in the art, modifications of the present invention can be made in view of the foregoing disclosure without departing from the spirit and scope of the invention.

We claim:

1. Apparatus for use in determining the amount of iron present in a used lubricating oil which comprises a reaction chamber having upper and lower ends; a closure member formed of a rubbery material adapted to close the lower end of the reaction chamber; a solid body member non-rotatably attached to the upper end of the reaction chamber, the said body member having a plurality of cavities formed therein with each of the cavities having a lower opening therein communicating the cavity with the reaction chamber; a rotatable top member having an opening therein positioned on the body member and rotatable relative thereto; and means for sequentially positioning an opening in the rotatable top member so that it is in vertical alignment with one of said plurality of cavities in the body member.

2. The apparatus according to claim 1 in which the reaction chamber and body member are cylindrical in shape and the body member has six equally spaced cavities formed therein adjacent to its periphery; the rotatable top member is circular in shape with two openings therein and a shaft is centrally attached to its underside and extends through an opening in the body member to a point below the underside of the body member; the positioning means comprises a ratchet wheel having six teeth attached to the lower end of the shaft and a pawl attached to the underside of the body member so that it cooperates with the teeth of the ratchet wheel; and a spring loaded plunger is positioned with its piston end located in one of the openings in the top member.

* * * * *